United States Patent [19]

Chabardes et al.

[11] Patent Number: 5,157,131
[45] Date of Patent: Oct. 20, 1992

[54] EPOXIDES AND A PROCESS FOR THEIR PREPARATION

[75] Inventors: Pierre Chabardes, Sainte Foy Les Lyon; Bernard Delmond, Pessac; Claude Filliatre; Michel Pereyre, both of Talence; Dominique Serramedan, La Rochelle, all of France

[73] Assignee: Rhone-Poulenc Nutrition Animale, Commentry, France

[21] Appl. No.: 779,496

[22] Filed: Oct. 24, 1991

[30] Foreign Application Priority Data

Oct. 25, 1990 [FR] France .................... 90 13250

[51] Int. Cl.$^5$ .................. C07D 303/04; C07D 301/16
[52] U.S. Cl. ......................... 549/332; 549/526
[58] Field of Search ................. 549/545, 546, 332

[56] References Cited

U.S. PATENT DOCUMENTS

| | | | |
|---|---|---|---|
| 2,863,882 | 12/1958 | Bain et al. | 549/546 |
| 3,023,224 | 2/1962 | Meyer et al. | 549/541 |
| 4,044,028 | 8/1977 | Rosenberger et al. | 549/332 |
| 4,721,798 | 1/1988 | Mulder | 549/545 |
| 4,933,477 | 6/1990 | Goetz et al. | 549/520 |
| 5,017,711 | 5/1991 | Chapuis et al. | 549/332 |
| 5,081,312 | 1/1992 | Chapuis et al. | 549/332 |

FOREIGN PATENT DOCUMENTS

| | | | |
|---|---|---|---|
| 374509 | 6/1990 | European Pat. Off. | 549/332 |
| 1098884 | 1/1968 | United Kingdom . | |

OTHER PUBLICATIONS

Josef Ehrenfreud et al., "Oxydation von Allylalkoholem mit Blei (IV)-Accetat", Halvetica Chimica Acta., vol. 57, No. 121, pp. 1098–1114, 1974.

Hans Meyer et al., "Synthese Von Optische ... ", Helvetica Chimica Acta., vol. 63, No. 153, pp. 1450–1455 (1980).

Primary Examiner—Joseph E. Evans
Attorney, Agent, or Firm—Finnegan, Henderson, Farabow, Garrett and Dunner

[57] ABSTRACT

Epoxides represented by the formula:

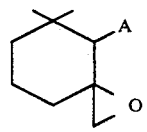

in which A represents a methylene or oxirane group and a process for their preparation.

1 Claim, No Drawings

EPOXIDES AND A PROCESS FOR THEIR PREPARATION

BACKGROUND OF THE INVENTION

The present invention relates to novel epoxides and particularly cyclic epoxides and a process for their preparation.

Epoxides having cyclic structures are known in the prior art. In particular, ErhenFreund et al. (Helv. Chim. Acta., 57(4), 1098 (1974)) have described the following epoxide (2a):

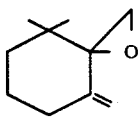
(2a)

obtained as by-product of the oxidation of β-cyclogeraniol by lead tetraacetate.

Rosenberger et al. (Helv. Chim. Acta., 63(6), 1665 (1980)) have described the position isomer of the double bond (2b) obtained by reacting 2,2,6-trimethylcyclohexanone with a sulphur ylide.

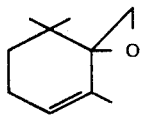
(2b)

SUMMARY OF THE INVENTION

The epoxides of the invention are represented by formula (1):

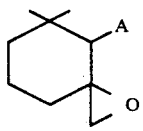
(1)

in which A represents a methylene (1a) or oxirane (1b) group.

Therefore, the compounds of the invention are:
5,5-dimethyl-4-methylene-1-oxaspiro[2.5]octane (1a); and
7,7-dimethyl-1,5-dioxadispiro[2.0.2.4]decane (1b).

These novel epoxides may be used as stabilizers for polyvinyl chloride (PVC). They may also be used as raw material for the synthesis of epoxy resins or as comonomers for the production of bonding agents in polymers.

The compounds of formula (1) of the invention may be prepared by epoxidation of a pyronene represented by formula (3):

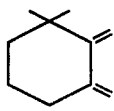
(3)

with an epoxidizing agent.

DESCRIPTION OF THE PREFERRED EMBODIMENTS

Reference will now be made in detail to the present preferred embodiments of the invention. In the examples and throughout the specification and claims, all parts and percentages are by weight unless otherwise specified.

Preferably, the epoxidation of the pyronene is carried out with an epoxidizing agent selected from peracids or their derivatives, hypohalous acids or their precursors, hydrogen peroxide, alkyl hydroperoxides, perborates or percarbonates.

The organic peracids which may be used in the present invention include optionally substituted aliphatic or aromatic carboxylic acids and acid derivatives. In particular, peracetic acid, performic acid, perpropionic acid, pertrifluoroacetic acid, para-nitroperbenzoic acid or meta-chloroperbenzoic acid may be used.

In one embodiment of the process of the invention, it is possible to directly synthesize the peracid "in situ" using a mixture of hydrogen peroxide and the corresponding acid. In this embodiment, the acid may be used in catalytic amounts since, during the reaction of the peracid with the pyronene, the starting acid is regenerated and may be recycled into a peracid by reaction with the hydrogen peroxide.

When hydrogen peroxide is one of the reactants, it may be used alone, in a basic medium or in combination with:
- a metal or,
- a nitrile (Radziszewski's reaction: Wiberg, J. Amer. Chem. Soc., 75, 3961 (1953)).

Metals which may be used in the process when hydrogen peroxide is used include transition metals such as tungsten, molybdenum, vanadium, titanium, platinum or manganese, any of which may be optionally combined with another metal such as tin. Preferably, tungsten, molybdenum or platinum is used as the transition metal.

In the case of hydroperoxides, the epoxidizing agent used is the combination ROOH+metal in which R is an alkyl radical and the metal is selected from transition metals such as vanadium, titanium, molybdenum, platinum or cobalt. Preferably, the hydroperoxide is represented by the formula:

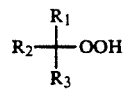

in which $R_1$ to $R_3$, which are identical or different, each independently represents:
- a hydrogen atom;
- a linear or branched alkyl group containing 1 to 30 carbon atoms;
- a cycloalkyl group containing 3 to 12 carbon atoms; or
- an alkyl- or cycloalkylaromatic group containing 7 to 30 carbon atoms.

Among the metals which may be used when the epoxidizing agent is an alkyl hydroperoxide, vanadium and titanium are preferred.

In the case of hypohalous acids, the epoxidizing agent are of the formula X—OH in which X may be Cl, Br or I. It is also possible to implement the process of the invention using any precursor of these acids and in particular halogen ion (+) generating precursors. These may be in particular sodium or potassium hypochlorite or hypobromite at slightly acid pH, or Cl or Br ions in the presence of water and at slightly acid pH or, alternatively, N-halogenated derivatives of amides such as N-bromosuccinimide or N-bromoacetamide also in the presence of water.

Examples of percarbonates and the perborates which may be used in the present invention include sodium percarbonate (Chem Letters 665 (1986)), sodium perborate (Tetrahedron Letters, 2967 (1988)) and alkyl perborates (FR 1,447,267), whose effect on the epoxidation of alkenes has been described.

The epoxidation reaction is carried out in an inert atmosphere in the presence of a solvent selected from:
  water;
  ethereal solvents such as ethyl ether or propyl ether, THF, or alternatively methyl tertbutyl ether;
  halogenated solvents such as chlorobenzenes, chloroform, methylene chloride or dichloropropane;
  aliphatic or aromatic hydrocarbons and in particular alkanes having more than 5 carbon atoms (hexane, heptane);
  organic acids such as acetic acid or formic acid;
  alcohols; or
  esters.

The various reagents may be introduced simultaneously, but the addition of the epoxidizing agent to the pyronene dissolved in the solvent is preferred.

Moreover, it is possible to add a phase transfer agent to the medium in order to carry out the catalysis by phase transfer. In particular, the following may be added:
  quaternary ammonium salts such as tetrabutylammonium hydroxide, bromide or chloride, methyltrioctylammonium chloride or dimethyl[dioctadecyl+dihexadecyl]ammonium chloride;
  aromatic or chlorinated hydrocarbons;
  phosphonium salts, such as hexadecyltributylphosphonium chloride;
  certain anionic complexes such as tetrahexylammonium tetra(diperoxotungsto)phosphate.

The reaction is advantageously carried out in an inert atmosphere at a temperature between $-30°$ C. and $+100°$ C., preferably between 0° C. and 50° C. It may be particularly advantageous to carry out the reaction at about room temperature.

The reaction conditions (temperature, nature of the solvent and the epoxidizing agent, and duration of the reaction) can be adjusted by a person skilled in the art to obtain the desired optimum reaction rate and to obtain the product sought.

In particular, the use of a hypohalous acid generally makes it possible to form the monoepoxide (1a), whereas the use of a peracid leads predominantly to the diepoxide (1b).

The molar ratio of epoxidizing agent/pyronene is advantageously between 0.5/1, and 1.5/1, when it is desired to prepare the compound (1a), and between 1.5/1, and 2.5/1, when it is desired to prepare the compound (1b).

When the two products are obtained simultaneously they may be separated, for example, by liquid phase chromatography.

During the preparation of the compounds of the invention, the epoxide of formula (2a) described by ErhenFreund (Helv. Chim. Acta., 57(4), 1098 (1974)) (Helv. Chim. Acta., 57(4), 1098 (1974)) is also formed.

The latter may be separated from the compounds of the invention, for example by liquid phase chromatography.

The starting pyronene (δ-pyronene) used in the present invention may be obtained by various means. In particular, it may be prepared from myrcene according to the following procedure disclosed in French Patent Application FR 9002724:
  bringing the myrcene into contact with sulphur dioxide in the presence of a polymerization inhibitor at a temperature of between 60° and 100° C. in order to form myrcenesulphone;
  treating the myrcenesulphone in the presence of a strong acid containing less than 5% of water in order to form cyclic sulpholene; and
  heating the cyclic sulpholene, optionally in the presence of a basic catalyst, to form the pyronene.

During the second stage, alkyl, aryl or halosulphonic acids, nafion resins, perchloric acid, sulphuric acid or various heterogeneous acid catalysts may be used as strong acids.

The compounds of the invention may be used as stabilizers for PVC or in the synthesis of resins or polymers.

The present invention will be more fully described by means of the following examples which should be considered as illustrative and nonrestrictive.

EXAMPLE 1

0.27 g (2 mmol) of δ-pyronene and 0.105 g of decane (internal standard) were placed in 11 ml of anhydrous ether at 0° C. in a 25-ml round-bottomed flask. 0.78 g (3.2 mmol) of 72% metachloroperbenzoic acid was added. The reaction mixture was allowed to equilibrate to room temperature and was stirred for 28 hours. The diepoxide formed was assayed by vapor phase chromatography using an internal standard.

0.11 g of diepoxide was thus obtained, representing a 33% yield. The diepoxide contained 2 isomers whose physicochemical data are as follows:

$^1$H NMR (CDCl$_3$)δ: 0.89 m (6H); 1.35 to 1.95 m (6H); 2.51 (2H); 2.64 (2H).

By using $^{13}$C NMR, the presence of two isomers was detected.

First isomer $^{13}$C NMR (CDCl$_3$)δ: 20.2 (CH$_2$); 22.9 (CH$_3$); 24.2 (CH$_3$); 32.1 (CH$_2$); 34.9 (Q); 38.1 (CH$_2$); 48.6 (CH$_2$); 52.4 (CH$_2$); 56.4 (Q); 61.7 (Q).

Mass m/Z (% relative intensity): 153 (M$^+$-CH$_3$, 9); 95 (100).

Second isomer $^{13}$C NMR (CDCl$_3$)δ: 20.2 (CH$_2$); 22.5 (CH$_3$); 24.5 (CH$_3$); 33.4 (CH$_2$); 35.1 (Q); 39.1 (CH$_2$); 46.7 (CH$_2$); 50.7 (CH$_2$); 57.9 (Q); 63.0 (Q).

Mass m/Z (% relative intensity): 153 (M$^+$—CH$_3$, 5); 95 (100).

EXAMPLE 2

2.27 g (0.013 mol) of N-bromosuccinimide in an acetone/water mixture: (9.4 ml/1.9 ml) were placed in a 20-ml round-bottomed flask under N$_2$ at 0° C. 1.5 g (0.011 mol) of δ-pyronene were added and the mixture was allowed to dissolve. When all of the N-bromosuccinimide had been dissolved, the mixture was extracted with ether, washed with a saturated solution of bicarbonate and dried over MgSO$_4$. After evaporation of the solvents, the crude reaction mixture was dissolved in 10 ml of absolute methanol, and 3.8 g of potassium carbonate (2.5 equivalents) were added at 0° C. under $N_2$.

After stirring for 45 minutes, the mixture was extracted with ether, washed with a 1N solution of HCl and then with a saturated solution of ammonium chloride until neutral. After evaporation of the solvents, the crude reaction mixture was purified on a deactivated alumina column by eluting with a solution of petroleum ether/ether: 9/1.

503 mg of monoepoxide of the formula:

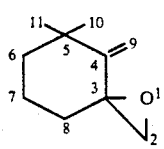

having the following physicochemical characteristics were thus obtained:

$^1$H NMR (CDCl$_3$)δ: 1.06 S (3H); 1.13 S (3H); 1.44 to 1.80 m (6H); 3.28 to 3.64 (2H); 4.74 to 4.96 (2H).

$^{13}$C NMR (CDCl$_3$)δ: 154.5 (C-4); 59.0 (C-3); 35.0 (C-8); 20.8 (C-7); 40.3 (C-6); 38.0 (C-5); 103.9 (C-9); 27.1 (C-10); 28.5 (C-11); 57.0 (C-2).

Mass m/Z (% relative intensity): 152 (M$^+$, 1.5); 84 (100).

It will be apparent to those skilled in the art that various modifications and variations can be made in the present invention without departing from the scope or spirit of the invention. Thus, it is intended that the present invention cover the modifications and variations of this invention provided they come within the scope of the appended claims and their equivalents.

What is claimed is:

1. A compound represented by the formula (1):

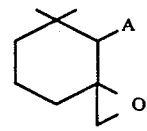

in which A represents a methylene or an oxirane group.

* * * * *